(12) United States Patent
Kutlu et al.

(10) Patent No.: US 10,342,790 B2
(45) Date of Patent: Jul. 9, 2019

(54) USE OF CERANIB-2 IN THE TREATMENT OF LUNG CANCER

(71) Applicant: ANADOLU UNIVERSITESI REKTORLUGU, Eskisehir (TR)

(72) Inventors: Hatice Mehtap Kutlu, Eskisehir (TR); Gokhan Kus, Eskisehir (TR)

(73) Assignee: ANADOLU UNIVERSITESI REKTORLUGU, Eskisehir (TR)

( * ) Notice: Subject to any disclaimer, the term of this patent is extended or adjusted under 35 U.S.C. 154(b) by 0 days.

(21) Appl. No.: 15/899,520

(22) Filed: Feb. 20, 2018

(65) Prior Publication Data
US 2018/0235951 A1 Aug. 23, 2018

(30) Foreign Application Priority Data

Feb. 20, 2017 (TR) .............................. a 2017 02500

(51) Int. Cl.
| | | |
|---|---|---|
| A61K 31/10 | (2006.01) | |
| A61K 31/40 | (2006.01) | |
| A61K 31/47 | (2006.01) | |
| A61K 31/70 | (2006.01) | |
| A61P 35/00 | (2006.01) | |
| A61K 31/337 | (2006.01) | |
| A61K 31/427 | (2006.01) | |
| A61K 31/506 | (2006.01) | |
| A61K 31/513 | (2006.01) | |
| A61K 31/517 | (2006.01) | |
| A61K 31/519 | (2006.01) | |
| A61K 31/565 | (2006.01) | |
| A61K 31/665 | (2006.01) | |
| A61K 31/704 | (2006.01) | |
| A61K 31/4188 | (2006.01) | |
| A61K 31/4704 | (2006.01) | |

(52) U.S. Cl.
CPC .......... *A61K 31/4704* (2013.01); *A61K 31/10* (2013.01); *A61K 31/337* (2013.01); *A61K 31/40* (2013.01); *A61K 31/4188* (2013.01); *A61K 31/427* (2013.01); *A61K 31/506* (2013.01); *A61K 31/513* (2013.01); *A61K 31/517* (2013.01); *A61K 31/519* (2013.01); *A61K 31/565* (2013.01); *A61K 31/665* (2013.01); *A61K 31/704* (2013.01); *A61P 35/00* (2018.01); *A61K 31/47* (2013.01); *A61K 31/70* (2013.01)

(58) Field of Classification Search
CPC ................................ A61K 31/47; A61K 31/70
USPC ........................................ 514/312, 49, 314
See application file for complete search history.

(56) References Cited

U.S. PATENT DOCUMENTS

| | | | | |
|---|---|---|---|---|
| 5,472,949 A | * | 12/1995 | Arasaki | C07H 19/06 514/49 |
| 6,534,524 B1 | * | 3/2003 | Kania | C07D 209/18 514/314 |

OTHER PUBLICATIONS

Vethakanraj et al., Targeting ceramide metabolic pathway induces apoptosis in human breast cancer cell lines, Biochemical and Biophysical Research Communications, vol. 464, No. 3, pp. 833-839 (2015).*

Draper, J. et al., "Discovery and Evaluation of Inhibitors of Human Ceramidase", Molecular Cancer Therapeutics, 10(11): 2052-2061 (2011).

\* cited by examiner

*Primary Examiner* — Kevin E Weddington

(74) *Attorney, Agent, or Firm* — Merchant & Gould P.C.

(57) ABSTRACT

The present invention relates to the use of ceranib-2 molecule in the treatment of lung cancer and breast cancer. At the same time, the present invention also describes the in vitro studies made by the inventors in this direction.

5 Claims, 2 Drawing Sheets

USE OF CERANIB-2 IN THE TREATMENT OF LUNG CANCER

Figure 1:
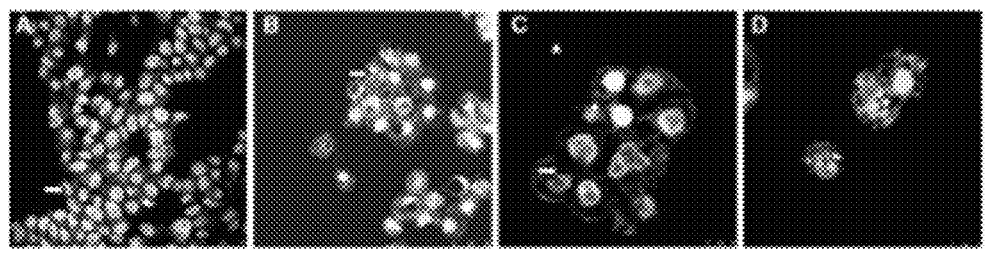

This application claims benefit of Serial No. TR 2017/02500, filed 20 Feb. 2017 in Turkey, and which application is incorporated herein by reference. To the extent appropriate, a claim of priority is made to the above disclosed application.

The present invention relates to the use of ceranib-2 molecule in the treatment of lung cancer and breast cancer. At the same time, the present invention also describes the in vitro studies made by the inventors in this direction.

KNOWN STATE OF THE ART

In the treatment of cancer and in chemotherapy stage, pluralities of different types of medicines are used and these medicines exhibit efficiencies by means of different effect mechanisms. These medicines, which are different in terms of pharmacological characteristics, are collected in seven main groups, namely, alkylating agents, anti-metabolites, antitumor antibiotics, nitrosoureas, vinco (plant) antibiotics and hormones.

Most of the antineoplastic medicines used frequently in cancer treatment shows effect by means of suppressing cell division and proliferation. In medicines having said effect mechanism, the efficiency of the used antineoplastic medicines is delimited since the effect of the medicine is unique for the specific period of the cell cycle and since depending on this, the medicine kills limited number of cells which are in the related cell cycle during the period where the medicine is applied to the body. In medicines having a different effect mechanism, the effect is realized in an independent manner from the rest and division conditions of the cells. However, as described here, a generic characteristic of the medicines which are not unique for the cell period and in other words, which are independent of the cell period is that they directly deteriorate the DNA structure.

Since the known chemotherapy agents have serious side effects, research studies have been made in the direction of development of different effect mechanisms and development of active substances which may show efficiency through these mechanisms.

The main targets in cancer treatment are the determination of different mechanisms which provide cell apoptosis and the determination of the enzymes which play an important role in this mechanism, and these targets are attractive for many researchers.

As a result of the researches made, it has been determined that ceramide, which is a bio-active lipid formed as a result of hydrolysis of sphingomyelin, plays an important role in some cell culture models, in stoppage of the cell cycle, in differentiation and in apoptosis, and when the cells are subjected to mitogen factors, the intracellular ceramide amount is decreased and ceramide amount increases when the intracellular ceramidase enzyme activity decreases. The increase of the ceramide amount results in apoptosis. Thus, it is considered that the molecules, which inhibit ceramidase enzyme, have high probability of anti-cancerogenic characteristic. In the light of this, some compounds which inhibit ceramidase activity have been developed, however, the pharmacological characteristics of them are not sufficient for cancer treatment.

Breast cancer and lung cancer are among the most frequent cancer types, and the resistance development of the patients against known chemotherapy agents prevents obtaining of the desired effect in the treatment. This necessitates the use of molecules, which show efficiency through novel and different effect mechanisms, in the treatment of these diseases.

OBJECT OF THE INVENTION

The inventors aim to develop a novel efficiency in biochemical way which is suitable for use in the treatment of breast cancer and lung cancer.

Another object of the present invention is to provide use of the molecules, which provide cell apoptosis by means of a different mechanism through the known apoptosis paths in breast cancer and lung cancer treatment, in the treatment of said diseases.

The inventors, who made studies in the direction of these objects, have found that the molecules which inhibit the ceramidase enzyme, particularly the ceranib-2 molecule is/are effective in the treatment of breast cancer and lung cancer.

DETAILED DESCRIPTION OF THE INVENTION

The present invention relates to the use of molecules which inhibit the ceramidase enzyme, preferably the use of ceranib-2 molecule in prevention, in the treatment of breast cancer and lung cancer or in the elimination the symptoms resulting from these diseases.

The statement of "breast cancer" used within the scope of the present invention describes that there are abnormal cells inside the breast tissue. Within the scope of the invention, the breast cancer may be in situ ductal carcinoma (DCIS), in situ lobular carcinoma (LCIS), invasive breast cancer, invasive (or infiltrative) ductal carcinoma, invazif (or infiltrative) lobular carcinoma, inflammatory breast cancer, paget's disease, medullary breast cancer, mucinosis breast cancer, tubular breast cancer, adenoid cystic breast cancer, metaplastic breast cancer, angio-carcinoma of the breast, basal type breast cancer, phyllodes or cysto-carcinoma phyllodes, papillary breast cancer. Said cancer types can be in any stage, for instance in stages I, II, III or IV or in the stages existing in the lower groups of them.

The statement of "lung cancer" used within the scope of the present invention describes the presence of abnormal cells in one lung or in both lungs and/or the uncontrolled growth of abnormal cells. Within the scope of the present invention, the lung cancer can be small cell lung cancer, lung cancer except small cell lung cancer, adeno cancer, squamous celled cancer, large celled cancer. Said cancer types can be in any stage, for instance, in stages I, II, III or IV or in the stages existing in the lower groups of them.

The statement of "the molecule which inhibits ceramidase enzyme" used within the scope of the present invention describes all molecules which stop or decelerate or differentiate the hydrolyze function of the ceramidase enzyme for the ceramide molecule.

The statement of "ceranib-2" used within the scope of the present invention covers the molecule described in Mol Cancer Ther. 2011 November; 10(11): 2052-2061 reference and the pharmaceutically acceptable derivatives of said molecule, for instance, the salts and/or pre-medicine forms and/or polymorphs.

Ceranib-2 is an inhibitor which inhibits ceramidase activity and which is not lipid. Its chemical name is 3-[3-(4-methoxyphenyl)-1-oxo-2-prpen-1-yl]-4-phenyl-2(1H)-quinolinone. Its formula is $C_{25}H_{19}NO_3$, and it is a white crystal structured powder whose molecular weight is 381.4 g/mole. The purity degree of the used material is greater than %98.

The statement of "treatment" used within the scope of the present invention describes the healing of patients by means of elimination of breast cancer and lung cancer and all types of these diseases defined within the scope of the invention.

The statement of "elimination of the symptoms resulting from breast cancer and lung cancer" used within the scope of the present invention describes elimination of at least one of the symptoms and/or disorders caused by said diseases.

From another perspective, the present invention covers usage of a method used in treatment of breast cancer and/or lung cancer inside a composition in a stand-alone manner or in a combined manner with another antineoplastic agent for ceranib-2 or for any molecule which inhibits ceramidase enzyme.

Another characteristic of the present invention is the use of molecules which inhibit ceramidase enzyme, preferably, ceranib-2 molecule with at least another antineoplastic agent, in the prevention, in the treatment of breast cancer and lung cancer or in elimination of the symptoms resulting from these diseases.

The antineoplastic agent mentioned here can be selected from a group comprising cyclo-phosphamide, iphosphamide, temozolomide, capecitabine, 5-floro uracil, methotrexate, gemcitabine, pemetrexed, mitomycin, bleomycin, epirubicin, doxorubicin, etoposide, paclitaxel, irinotecan, docetaxel, vincristine, carboplatin, cisplatin, oxaliplatin, bevacizumab, cetuximab, gefitinib, imatinib, trastuzumab, denosumab, rituximab, sunitinib, zoledronat, abirateron, anastrozole, bicalutamide, exemestane, goserelin, medroxy-progesterone, octreotide, tamoxifen, bendamustine, carmustine, chlorambucil, lomustine, melphalan, procarbazine, streptozosin, fludarabine, raltitrexed, actinomycin D, dactinomycin, doxorubicin, mitoxantrone, eribulin, topotecan, vinblastine, vinorelbine, afatinib, aflibercept, crizotinib, dabrafenib, interferon, ipilimumab, lapatinib, nivolumab, panitumumab, pembrolizumab, pertuzumab, sorafenib, trastuzumab emtansin, temsorilimus, vemurafenib, ibandronic acid, pamidronate, bexarotan, buserelin, cyproterone, degarelix, folinic acid, fulvestrant, lanreotide, lenalidomide, letrozole, leuproreline, megestrol, mesna, thalidomide or from the double or triple combinations of them.

Another characteristic of the present invention is the use of molecules which inhibit ceramidase enzyme, preferably, ceranib-2 molecule with a dose in the range of 1 µg/kg and 1 g/kg, in the prevention, in the treatment of breast cancer and lung cancer or in elimination of the symptoms resulting from these diseases.

Another characteristic of the present invention is the use of molecules which inhibit ceramidase enzyme, preferably, ceranib-2 molecule with a pharmaceutical dosage form, in the prevention, in the treatment of breast cancer and lung cancer or in elimination of the symptoms resulting from these diseases.

In another application of the present invention, in case ceranib-2 molecule is used together with/in a combined form together with at least one other antineoplastic agent, said compounds can be formulated together or in separate forms and said at least one antineoplastic agent can be in the same or different dosage forms as ceranib-2.

Said pharmaceutical dosage form can be any one of the conventional dosage forms known in the art, for instance, in tablet or capsule forms suitable for applying orally or in liquid forms suitable for intravenous, intra-peritoneal, intra-muscular, subcutaneous, etc. applications or it can be in ointment, cream, spray, etc. forms suitable for topical application.

The formulations comprising the ceranib-2 molecule of the present invention may optionally comprise at least one pharmaceutically acceptable auxiliary substance.

Now, the present invention will be described with reference to the examples below which are only for exemplary purposes and which shall not be interpreted to delimit the scope of the present invention in any manner.

EXAMPLES

Example 1: MTT Cyto-Toxicity Test

A549 human lung adeno-carcinoma cells have been implanted to the cell culture plates with 96 wells such that there are $2 \times 10^3$ cells per well. The cells implanted to the plate have been incubated at 37° C. and in a medium of 5% carbon dioxide. A549 cells have been incubated for 24 hours in the concentration range of 5-65 µM with synthesized ceranib-2. At the end of the duration, 20 µL MTT dye (5 mg/mL) has been added to each well and it has been incubated for 2 hours more at 37° C. After the incubation, the liquid part in each well on the plate is discharged and 200 µL DMSO has been added for dissolving the formazan salts formed by viable cells and it has been waited for 10 minutes at room temperature. The color change occurring has been read at wavelength of 570 nm on the ELx808-IU (Bio-Tek, USA) plate reader. The experiment has been repeated 3 times. Separate viability values have been calculated according to the control group for each dose.

RESULTS AND EVALUATION

In the studies made, IC50 concentration of ceranib-2 in MCF-7 human breast cancer cells has been detected as 13 µM, it has been detected as 14 µM in A549 lung cancer cells and it has been detected as 3 µM in 5RP7 cells and as 5 µM in NIH/3T3 cells. In the sources, when it is taken into consideration that the $IC_{50}$ concentration in cell-based experiments is mentioned approximately as 28 µM, it has occurred as a result of the studies that this molecule has unexpected high efficiency in MCF-7 cells. Moreover, in the in vivo studies made, 20-50 mg/kg ceranib-2 inhibits tumor growth in the synergistic tumor model without leading to toxicity.

In FIG. 1, the confocal microscopy images are provided belonging to the study made on the MCF-7 cell line. In the control cells, a tight and normal cell and cell nucleus structure are seen (FIG. 1A). In the cells treated with ceranib-2 for 24 hours, condensation is observed in the chromatin, holes are observed in the cell structure, shrunken cell nucleus is observed and fragmentizing cells are observed. This shows that ceranib-2 has a substantially high effect on this cell line.

Figure 2:
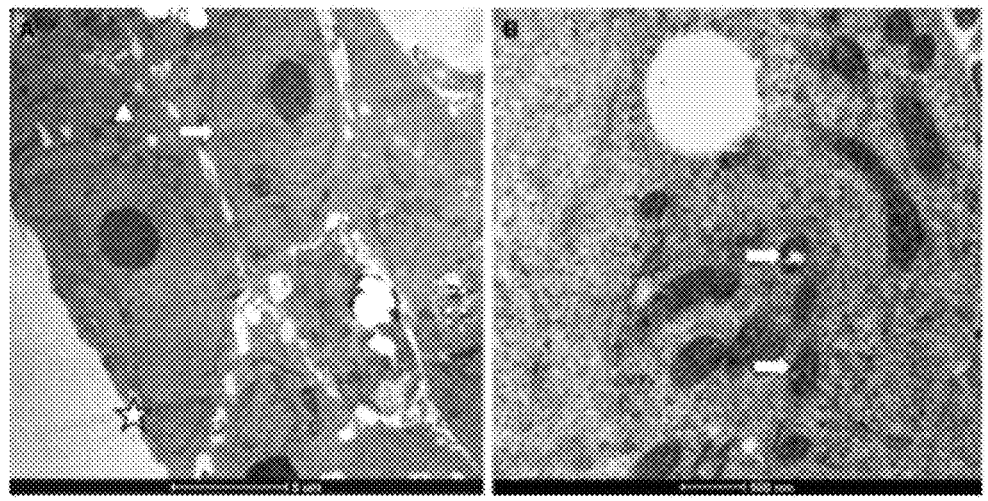

In FIG. 2, electron micrographs of the MCF-7 cells are seen. The cell membrane, nucleus membrane and mitochondria structure of the control group are preserved and it has been observed that in the cells treated with ceranib-2 for 24 hours, the nucleus membrane is lost and the mitochondria is deformed.

Figure 3:
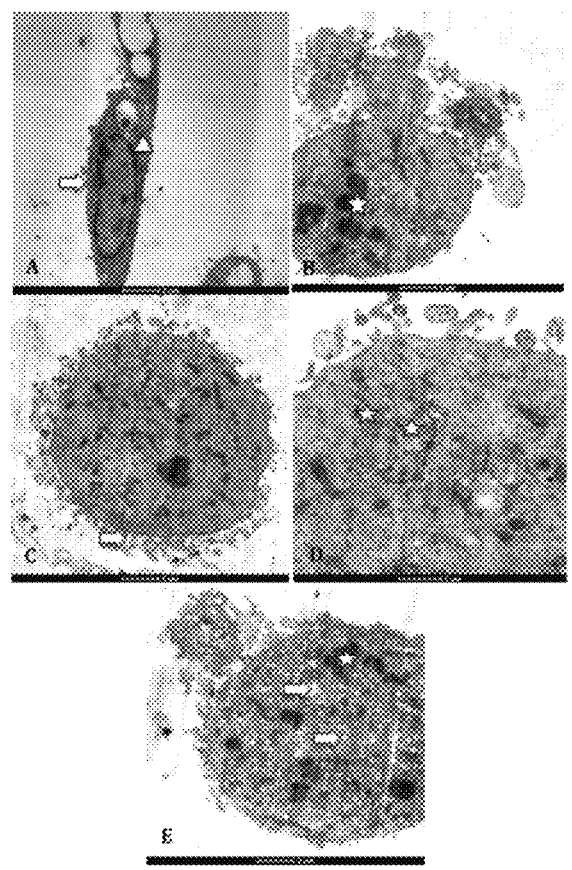

In FIG. 3, the confocal microscope images of the study made on A549 type cells which is a lung cancer cell line are given. In FIG. 3A, while it has been observed that the control group cells preserve important structures for cell viability like the cell membrane, nucleus membrane and mitochondria, it has been observed that in the same type of cells treated with ceranib-2 for 24 hours, the cell nucleus is fragmentized, the cell shape is transformed from oval to round and deformations begin in the cell membrane, lipid drops are formed inside the cell, DNA fragmentizing occurs and holes occur inside the cell. These experiment results show that the ceranib-2 molecule is effective on lung cancer.

Brief descriptions of figures shown as reference within the scope of the present invention are given below.

FIG. 1: Confocal electron transmission microscope image of MCF-7 cells painted with acridine orange and phalloidine. A) shows the control group; B), C) and D) show the cells treated with ceranib-2 for 24 hours.

FIG. 2: Electron transmission micrographs of MCF-7 cells. A) shows the control group; B) shows the cells treated with ceranib-2 for 24 hours.

FIG. 3: Electron transmission microscope images showing the structural changes in A549 cells. A) shows the control group; B), C), D) and E) show the cells treated with ceranib-2 for 24 hours.

The invention claimed is:

1. A method for treating lung cancer, or eliminating the symptoms resulting from lung cancer, the method comprising using ceranib-2.

2. The method of claim 1, wherein the lung cancer is small cell lung cancer, lung cancer except small cell lung cancer, adeno cancer, squamous celled cancer or large celled cancer.

3. The method of claim 1, wherein ceranib-2 is used together with at least one other antineoplastic agent.

4. The method of claim 3, wherein the other antineoplastic agent is selected from a group comprising cyclo-phosphamide, iphosphamide, temozolomide, capecitabine, 5 fluorouracil, methotrexate, gemcitabine, pemetrexed, mitomycin, bleomycin, epirubicin, doxorubicin, etoposide, paclitaxel, irinotecan, docetaxel, vincristine, carboplatin, cisplatin, oxaliplatin, bevacizumab, cetuximab, gefitinib, imatinib, trastuzumab, denosumab, rituximab, sunitinib, zoledronat, abirateron, anastrozole, bicalutamide, exemestane, goserelin, medroxy-progesterone, octreotide, tamoxifen, bendamustine, carmustine, chlorambucil, lomustine, melphalan, procarbazine, streptozosin, fludarabine, raltitrexed, actinomycin D, dactinomycin, doxorubicin, mitoxantrone, eribulin, topotecan, vinblastine, vinorelbine, afatinib, aflibercept, crizotinib, dabrafenib, interferon, ipilimumab, lapatinib, nivolumab, panitumumab, pembrolizumab, pertuzumab, sorafenib, trastuzumab emtansin, temsorilimus, vemurafenib, ibandronic acid, pamidronate, bexarotan, buserelin, cyproterone, degarelix, folinic acid, fulvestrant, lanreotide, lenalidomide, letrozole, leuproreline, megestrol, mesna, thalidomide or from the double or triple combinations of them.

5. The method of claim 1, wherein ceranib-2 is used at a dose between 1 µg/kg and 1 g/kg.

* * * * *